United States Patent [19]

Nakamura et al.

[11] Patent Number: 5,753,242
[45] Date of Patent: May 19, 1998

[54] EXTERNAL SKIN TREATMENT COMPOSITION

[75] Inventors: Fumiaki Nakamura; Yoshimaru Kumano; Kenzo Ito, all of Yokohama, Japan

[73] Assignee: Shiseido Company, Ltd., Tokyo, Japan

[21] Appl. No.: 712,293

[22] Filed: Sep. 11, 1996

Related U.S. Application Data

[62] Division of Ser. No. 468,504, Jun. 6, 1995, abandoned, which is a continuation of Ser. No. 250,143, May 27, 1994, abandoned.

[30] Foreign Application Priority Data

May 2, 1994 [JP] Japan ......................... 6-93500

[51] Int. Cl.$^6$ ........................................... A61K 7/00
[52] U.S. Cl. ........................................... 424/401; 514/844
[58] Field of Search .......................... 424/401; 514/844, 514/848

[56] References Cited

U.S. PATENT DOCUMENTS

| | | | |
|---|---|---|---|
| 4,774,016 | 9/1988 | Gazzani | 252/170 |
| 5,165,915 | 11/1992 | Tokubo | 424/63 |
| 5,221,796 | 6/1993 | Mori | 554/79 |
| 5,310,555 | 5/1994 | Ziegler | 424/601 |

FOREIGN PATENT DOCUMENTS

| | | |
|---|---|---|
| 0084341 | 7/1983 | European Pat. Off. . |
| 0349150 | 1/1990 | European Pat. Off. . |
| 0419148 | 3/1991 | European Pat. Off. . |
| 9001323 | 2/1990 | WIPO . |

*Primary Examiner*—Gollamudi S. Kishore
*Attorney, Agent, or Firm*—Sprung Kramer Schaefer & Briscoe

[57] ABSTRACT

An external skin treatment composition comprising erythritol, hydrogenated lecithin, and a polyoxyethylene-added cholesterol derivative, which is superior in prevention and improvement of skin roughness, with little sticky feeling, with quick absorption into the skin, and superior in the softening effect on the corneum.

12 Claims, 1 Drawing Sheet

EXTERNAL SKIN TREATMENT COMPOSITION

This is a division of application Ser. No. 08/468,504, filed Jun. 6, 1995 now abandoned, which is a continuation of application Ser. No. 08/250,143, filed on May 27, 1994 now abandoned.

FIELD OF THE INVENTION

The present invention relates to an external skin treatment composition which improves skin roughness, is quickly absorbed into the skin, softens the stratum corneum, and is superior in a moisturizing effect.

DESCRIPTION OF THE RELATED ART

One of the main purposes of external skin treatment compositions such as cosmetics is the prevention and improvement of skin roughness. To achieve this purpose, in the past the practice has been to formulate various humectants such as glycerol, sorbitol, propylene glycol, polysaccharides.

However, there is the problem that humectants such as polysaccharides, precipitate in formulations with large alcohol contents. Glycerol, sorbitol, propylene glycol, chondroitin sulfuric acid, and the like cause stickiness and a burning sensation when formulated in too much. In the case of amino acids such as DL-threonine cause the problems of discoloration or generation of foreign odors.

SUMMARY OF THE INVENTION

Accordingly, the objects of the present invention are to eliminate the above-mentioned problems of the conventional external skin treatment composition and to provide an external skin treatment composition capable of improving skin roughness, of being quickly absorbed into the skin, of softening the stratum corneum and of being superior in moisturizing effect.

Other objects and advantages of the present invention will be apparent from the following description.

In accordance with the present invention, there is provided an external skin treatment composition comprising erythritol, hydrogenated lecithin, and a polyoxyethylene-added cholesterol derivative.

BRIEF DESCRIPTION OF THE DRAWING

The present invention will be better understood from the description set forth below with reference to the accompanying FIG. 1, which is a graph showing the results of measurement of the softening effect on the stratum corneum by the external skin treatment composition according to the present invention.

DESCRIPTION OF THE PREFERRED EMBODIMENTS

Figure 1:
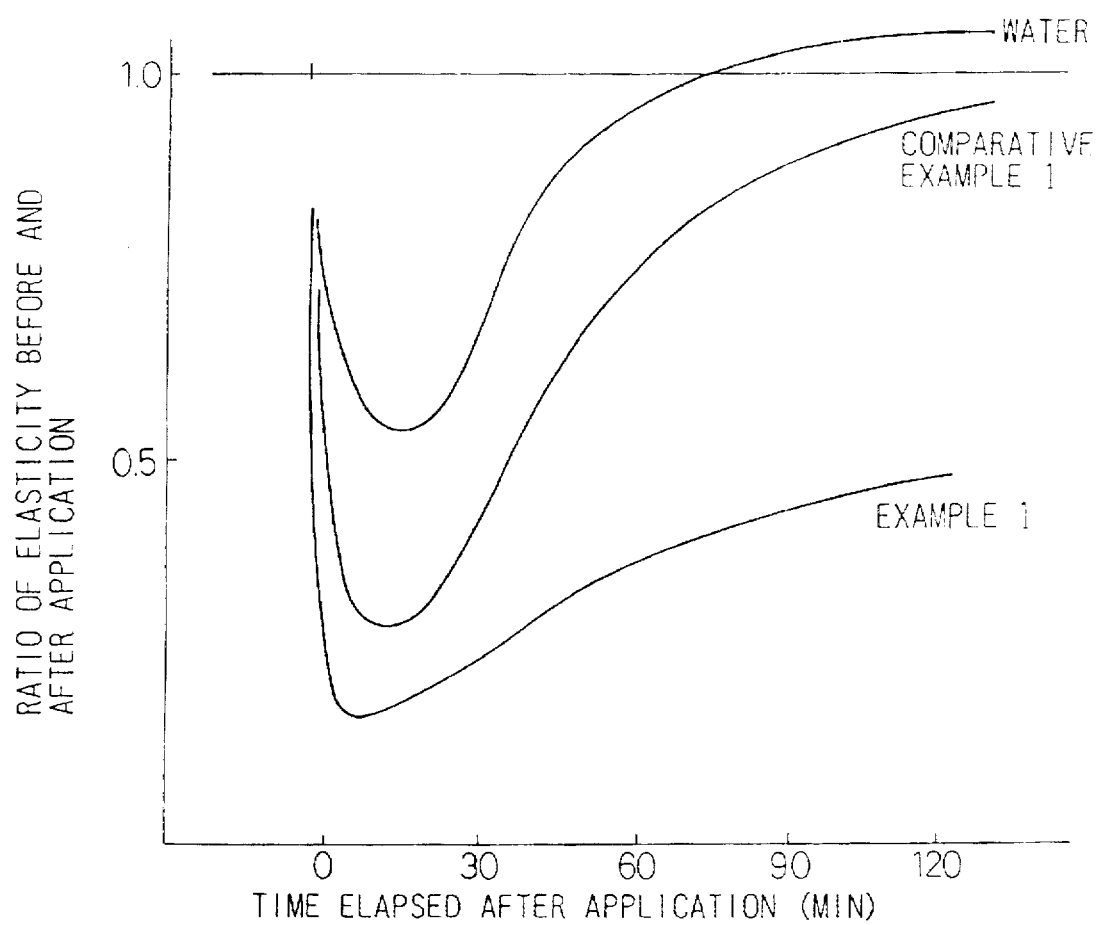

The present inventors, in consideration of the above situation, engaged in repeated in-depth studies and as a result found that an external skin treatment composition composed of a mixture of erythritol, hydrogenated lecithin, and a polyoxyethylene-added cholesterol derivative not only is superior in the prevention and improvement of skin roughness, but also is small in the stickiness observed in the case of in glycerol, sorbitol, and other polyhydric alcohols, is quickly absorbed into the skin, and is superior in the softening effect of the stratum corneum and thus completed the present invention.

The present invention will now be explained in further detail.

The erythritol usable in the present invention is also called meso-erythritol and is a sugar alcohol of tetrasaccharide contained in liche, basidium, fruit, and the like in the natural world.

The amount of the erythritol formulated in the present invention is preferably 0.1 to 30% by weight based on the weight of the external skin treatment composition, more preferably 0.5 to 20% by weight. When this amount is less than 0.1% by weight, the effect of improving skin roughness and moisturization is difficult to obtain. Conversely, when the amount is more than 30% by weight, no further increase can be expected in the effect of improvement of skin roughness and moisturization.

The hydrogenated lecithins usable in the present invention are, for example, phospholipids extracted from egg yolk, soybeans, corn, rapeseed, etc. and hydrogenated by a conventional method. However, to obtain white, odorless, good quality lecithin by hydrogenation, it is necessary to use lecithin which has not been oxidized or brownized when hydrogenized.

The amount of the hydrogenated lecithin to be formulated in the present invention is preferably 0.0001 to 1% by weight, based on the weight of the external skin treatment composition, more preferably 0.0005 to 0.5% by weight. With an amount less than 0.0001% by weight, the quickness of absorption into the skin and the effect of softening the stratum corneum are difficult to obtain. Conversely, when the amount is more than 1% by weight, no further increase can be expected in the quickness of absorption into the skin and the effect of softening the stratum corneum.

As the polyoxyethylene-added cholesterol derivative usable in the present invention, mention may be made of polyoxyethylene-added cholestanolether, polyoxyethylene-added phytosterolether, etc. The preferable addition mole, number of the polyoxyethylene is 5 to 70 moles. Especially, the use of polyoxyethylene (30 mole added) cholesterol is most preferable in view of the effect.

The amount of the polyoxyethylene-added cholesterol derivative formulated in the present invention is preferably 0.0001 to 1% by weight, more preferably 0.0005 to 0.5% by weight, based on the weight of the external skin treatment composition. When the amount is less than 0.0001% by weight, the quickness of absorption into the skin and the effect of softening the stratum corneum are difficult to obtain. Conversely, when the amount is more than 1% by weight, no further increase can be expected in the quickness of absorption into the skin and the effect of softening the stratum corneum.

The external skin treatment composition of the present invention may include, in addition to the above-mentioned essential components, other ingredients generally used in the other cosmetics, pharmaceuticals, and other external skin treatment compositions so long as the desired effects of the present invention are not impaired.

As such ingredients, it is possible to formulate, for example, powder components such as titanium dioxide, mica, and talc, oils such as avocado oil, macademia nut oil, corn oil, olive oil, rapeseed oil, evening primrose oil, castor oil, sunflower oil, tea seed oil, rice bran oil, jojoba oil, cacao fat, palm oil, squalene, squalane, beef tallow, Japanese tallow, beeswax, candelila wax, carnauba wax, spermiceti, lanolin, silicone oil, liquid paraffin, ceresine, and vaseline, higher alcohols such as capryl alcohol, lauryl alcohol, myristyl alcohol, cetyl alcohol, and phytosterol, higher aliphatic acids such as capric acid, lauric acid, myristic acid, palmic acid, stearic acid, behenic acid, lanolin fatty acid, linoleic acid, and linolenic acid, UV absorbents such as paraamino benzoic acid, homomenthyl-7N-acetyl-alantolanylate, butylmethoxydibenzoylmethane, di-p-methoxycinnamic acid-mono-2-ethylhexanoic acid glyceryl, amylsalicylate, octylmethoxycinnamate, and 2-hydroxy-4-methoxybenzophenone, moisture retainers such as polyethylene glycol, glycerol, sorbitol, xylitol, maltitol, mucopolysaccharide, hyaluronic acid, chondoroitin sulfate, and chitosan, thickeners such as methylcellulose, ethylcellulose, arabia gum, polyvinylalcohol, montmorillonite, and laponite, organic solvents such as ethanol and 1,3-butylene glycol, anti-oxidants such as butylhydroxytoluene, tocopherol, and phytic acid, antibacterial preservatives such as benzoic acid, salicylic acid, sorbic acid, alkyl esters of p-oxybenzoic acid (ethylparabene, butylparabene, etc.), and hexachlorophene, amino acids such as glycine, alanine, valine, leucine, serine, threonine, phenylalanine, tyrosine, asparagic acid, asparagine, glutamine, alginine, and hystidine and alkali metal salts thereof and hydrochlorides thereof, organic acids such as acylsarcosinic acid (for example, lauroylcosin sodium), glutathione, citric acid, malic acid, tartaric acid, and lactic acid, vitamin B's such as vitamin A and its derivatives, vitamin $B_6$ hydrochloride, vitamin $B_6$ tripalmitate, vitamin $B_6$ dioctanoate, vitamin $B_2$ and its derivatives, vitamin $B_{12}$, and vitamin $B_{15}$ and its derivatives, vitamin C's such as ascorbic acid, ascorbic acid sulfate (salts), ascorbic acid phosphate (salts), and ascorbyl dipalmitate, vitamin E's such as α-tocopherol, β-tocopherol, γ-tocopherol, vitamin E acetate, and vitamin E nicotinate, vitamin D's, vitamin H, vitamins such as pantotenic acid and pantetine, drugs such as nicotinic acid amide, nicotinic acid benzyl, γ-oryzanol, alantoin, glycyrrhizic acid (salts), glycyrrfietiric acid and its derivatives, hinokitiol, musidine, bisabolol, eucalyptol, thymol, inositol, saponins (saikosaponin, ginseng saponin, dishcloth gourd saponin, mukuro disaponin), pantothenylethylether, ethynylestradiol, tranexamic acid, cepharantine, and placenta extract, organic solvents for rumex japonicus, sophora flavescens, nupharis rhizoma, orange, sage, milfoil, mallow, cnidium rhizome, swertia herb, thyme, Japanese angelica root, bitter orange peel, birch, field horsetail, dishcloth gourd, horse chestnut, creeping saxifrage, arnica, lily, mugwort, herbaceous peony, aloe, Cape jasmine, and saware cypress; natural extracts extracted by alcohol, polyhydric alcohols, water, aqueous alcohols, etc., dyes, nonionic surface active agents such as sorbitan monolaurate, sorbitan monopalmitate, sorbitan sequioleate, sorbitan trioleate, polyoxyethylene sorbitan monolaurate, polyoxyethylene sorbitan monostearate, polyethylene glycol monooleate, polyoxyethylene alkyl ether, polyglycol diester, lauroyl diethanol amide, aliphatic acid isopropanol amide, maltitol hydroxy aliphatic ether, alkylated polysaccharides, alkyl glucoside, and sugar esters, cationic surface active agents such as stearyltrimethyl ammonium chloride, chloride benzalconium, and laurylamine oxide, anionic surface active agents such as sodium palmitate, sodium laurate, sodium laurosulfate, potassium laurosulfate, alkyl sulfuric acid triethanolamine ether, scopolia oil, linear dodecylbenzene sulfonate, polyoxyethylene hydrogenated castor oil malonate, acylmethyltaurine, bipolar surface active agents, perfumes, purified water, etc.

The external skin treatment compositions of the present invention can include, for example, a preparation such as cosmetics, pharmaceuticals, and quasi-drugs which are applied to the external skin and accordingly may take the form of any preparation and a wide variety of types such as an aqueous solution type, a soltibilized type (for example, lotion), an emulsion type (for example, an emulsion or cream), a powder type (for example, a foundation), a dispersion type, an oil-in-water type, a gel, an application, a two-layer water and oil type, a two-layer water and powder type, or a three-layer water, oil, and powder type.

EXAMPLES

The present invention will now be further illustrated by, but is by no means limited to, the following Examples.

Example 1

| Component | % by weight |
|---|---|
| Erythritol | 10 |
| Hydrogenated lecithin | 0.5 |
| Polyoxyethylene (30) cholestanolether | 0.5 |
| Water | 89 |

(Method of Production)

A 100 g amount of erythritol, 5 g of hydrogenated lecithin, and 5 g of polyoxyethylene (30) cholestanolether were dissolved in warm water, followed by adding water to give a total weight of 1000 g.

Comparative Example 1

| Component | % by weight |
|---|---|
| Erythritol | 10 |
| Water | 90 |

Comparative Example 2

| Component | % by weight |
|---|---|
| Hydrogenated lecithin | 0.5 |
| Polyoxyethylene (30) cholestanolether | 0.5 |
| Water | 99 |

Evaluation Example

The moisture retention effect, quickness of absorption into the skin, softening effect on corneum, and skin improving effect of an aqueous solution of erythritol, hydrogenated lecithin, and polyoxyethylene (30) cholestanolether (Example 1), an aqueous solution solely containing erythritol (Comparative Example 1), and an aqueous solution of hydrogenated lecithin and polyoxyethylene (30) cholestanolether (Comparative Example 2) were compared.

Measurement of Moisture Retention Effect by Moisture Evaporation Rate

As the test for measuring the moisture retention effect, measurement of the moisture evaporation rate is suitable. That is, 10 μl of a sample solution is dropped on 2.0×2.0 cm filter paper, then the reduction in weight is measured every minute until the 10th minute and the reduction in weight per minute is found. As a control, use was made of distilled water. Note that the value of the moisture evaporation rate for water was made "1".

The results are shown in Table 1. As clear from the results of Table 1, the synergistic effect was observed by the combination of erythritol, hydrogenated lecithin, and polyoxyethylene (30) cholestanolether according to the present invention.

TABLE 1

Moisture Evaporation Rate

| Sample | Moisture evaporation rate |
| --- | --- |
| Water | 1.00 |
| Comparative Example 1 | 0.90 |
| Comparative Example 2 | 0.98 |
| Example 1 | 0.83 |

Measurement of Absorption into Skin

As the test for measuring the skin absorption effect, measurement of the contact angle with the skin is suitable. That is, 5 μl of a sample was dropped on the skin, then the angle between the drops and the skin (contact angle) after three minutes was measured. The results are shown in Table 2. As shown in Table 2, the absorption was observed to be improved.

The sample was the same type as that used for the measurement of the moisture retention effect.

TABLE 2

Absorption into Skin

| Sample | Contact angle |
| --- | --- |
| Water | 105° |
| Comparative Example 1 | 103° |
| Example 1 | 51° |

Measurement of Softening Effect on Stratum Corneum

The softening effect on the stratum corneum was measured by coating 2 μl of an aqueous test solution on a 20 mm×5 mm corneum piece and then measuring the elasticity using a dynamic viscoelasticity measurement apparatus made by Toyo Seiki. The softening effect was expressed by the ratio Et/E of the elasticity at the time t after coating of the aqueous test solution with respect to the elasticity (E) of the corneum measured as the control.

The results are shown in FIG. 1.

As is clear from FIG. 1, the softening effect on the corneum is also increased by the combination of erythritol, hydrogenated lecithin, and polyoxyethylene (30) cholestanolether according to the present invention.

Action of Preventing Skin Roughness Caused by Application of Sodium Dodecyl Sulfate Next, a test was made on erythritol and glycerol, which have a moisture retention effect, to determine their action of preventing skin roughness with respect to stimulus caused by sodium dodecyl sulfate. That is, the skin at the inside of the lower arms of 10 health male subjects was treated with a 3% aqueous solution of sodium dodecyl sulfate to cause skin roughness. After 2 hours, 40 μl of each of the samples was coated and maintained in an open state. The skin roughness was caused and samples coated repeatedly over five days. On the sixth day, the state of the skin roughness was visually measured. The evaluation criteria are shown in Table 3 and the results are shown in Table 4.

TABLE 3

| Criteria for Evaluation of Skin Roughness | | |
| --- | --- | --- |
| Score | Evaluation | Remarks |
| 1 | Drying of wide range of corneum, peel-of, and strong erythema are observed. | Rough skin |
| 2 | Drying of corneum, peel-of, and medium degree of erythema are observed. | ↑ |
| 3 | Drying of corneum can be observed, but no peel-of. Weak erythema are observed. | |
| 4 | No drying of corneum and peel-of can be observed, but some erythema are observed. | ↓ |
| 5 | No drying of corneum, peel-of, or erythema can be observed. | Beautiful skin |

The judgement was made using the average value of the scores for 10 subjects.

Judgement of Skin Roughness

Excellent: Average score is from 4 to 5
Good: Average score is from 3 to less than 4
Fair: Average score is from 2 to less than 3
Poor: Average score is from 1 to less than 2

TABLE 4

| Action for Preventing Skin Roughness | |
| --- | --- |
| Sample | Action preventing skin roughness |
| Water | Poor |
| 10% glycerol | Good |
| Comparative Example 1 | Good |
| Example 1 | Excellent |

In the above way, a skin roughness preventing action is observed in both glycerol and erythritol, but it is clear that the synergistic effect is exhibited by combination of hydrogenated lecithin and polyoxyethylene (30) cholestanolether with erythritol.

Test of Actual Use

The results of improvement of skin roughness according to a test of actual use are shown below:

Test Method

The surface conditions of the skin of healthy female subjects (face) were observed by under a microscope (17X) by taking replicas of the skin using the silicone resin replica method. That is, use was made of a group of 30 subjects (skin roughness panel) judged from the skin surface micro-topograph and state of peeling of the corneum as having a skin roughness evaluation of 1 or 2 based on the criteria shown in Table 3 and the lotions of Example 1 and Comparative Example 1 were applied two times a day half and half on the left and right of the face. After two weeks, replicas were once again taken and the state of the skin was examined and evaluated in the same way as mentioned above in accordance with the criteria shown in Table 5.

TABLE 5

Criteria for Evaluation of Skin Roughness

| Score | Evaluation | Remarks |
|---|---|---|
| 1 | Disappearance of grooves and ridges peel-off of wide range of corneum | Rough skin |
| 2 | Unclear grooves and ridges, peel-off of corneum | ↑ |
| 3 | grooves and ridges are observed, but flat | |
| 4 | grooves and ridges are clear | ↓ |
| 5 | grooves and ridges are clear and well arranged | Beautiful skin |

The judgement was made using the scores by the following criteria:

Good: Ratio of panel giving score of 4 and 5 at least 75%

Fair: Ratio of panel giving score of 4 and 5 from 25% to less than 75%

Poor: Ratio of panel giving score of 4 and 5 less than 25%

Example 2

A lotion composed of the composition of Table 6 was produced by a conventional method and evaluated in accordance with the above-mentioned method.

TABLE 6

Lotion

| Component | Example 2 |
|---|---|
| Erythritol | 2.0% |
| Propylene glycol | 1.0 |
| Citric acid | 0.2 |
| 95% ethanol | 10.0 |
| Perfume | q.s. |
| Hydrogenated lecithin | 0.1 |
| Polyoxyethylene (30) cholestanolether | 0.1 |
| Purified water | Balance |
| Effect of improvement of skin roughness | Good |
| Absorption into skin | Good |

Comparative Example 3

A lotion composed of the composition of Table 7 was produced by a conventional method and evaluated in accordance with the above-mentioned method.

TABLE 7

Lotion

| Component | Comparative Example 3 |
|---|---|
| Glycerol | 2.0% |
| Propylene glycol | 1.0 |
| Citric acid | 0.2 |
| 95% ethanol | 10.0 |
| Perfume | q.s. |
| Purified water | Balance |
| Effect of improvement of skin roughness | Fair |
| Absorption into skin | Fair |

As clear from the results of Tables 6 and 7, the external skin treatment composition of the present invention is a novel external skin treatment composition superior in the effect of improving of skin roughness and absorption into the skin.

Example 3: Nourishing Cream

A nourishing cream was produced by a conventional method in accordance with the following formula:

| Component | % by weight |
|---|---|
| Stearic acid | 2.0 |
| Stearyl alcohol | 7.0 |
| Reduced lanolin | 2.0 |
| Squalane | 5.0 |
| Octyl dedecanol | 6.0 |
| Maltitol hydroxylaurylether | 3.0 |
| Glyceryl monostearate | 2.0 |
| Preservative | q.s. |
| Perfume | q.s. |
| Propylene glycol | 5.0 |
| Erythritol | 2.0 |
| Hydrogenated lecithin | 0.5 |
| Polyoxyethylene (30) cholestanolether | 0.5 |
| Potassium hydroxide | 0.2 |
| Purified water | Balance |

Example 4: Emulsion

An emulsion was produced by a conventional method in accordance with the following formula:

| Component | % by weight |
|---|---|
| Stearic acid | 2.0 |
| Cetanol | 1.0 |
| Vaseline | 3.0 |
| Lanolin alcohol | 2.0 |
| Liquid paraffin | 8.0 |
| Squalane | 2.0 |
| Octyl methoxycinnamate | 2.0 |
| Erythritol | 10.0 |
| Hydrogenated lecithin | 0.5 |
| Polyoxyethylene (30) cholestanolether | 0.5 |
| Polyoxyethylene (10) monooleate | 2.5 |
| Triethanol amine | 1.0 |
| Propylene glycol | 5.0 |
| Preservative | q.s. |
| Perfume | q.s. |
| Purified water | Balance |

Example 5: Rinse-Off Mask

A rinse-off mask was produced by a conventional, method in accordance with the following formula:

| Component | % by weight |
|---|---|
| Glycerol | 5.0 |
| Dipropylene glycol | 20.0 |
| Ethanol | 5.0 |
| Carboxyvinyl polymer | 1.0 |
| Erythritol | 5.0 |
| Hydrogenated lecithin | 0.1 |
| Polyoxyethylene (30) cholestanolether | 0.1 |
| Polyethylene powder | 3.0 |
| Potassium hydroxide | 0.4 |
| Preservative | q.s. |
| Perfume | q.s. |
| Purified water | Balance |

The external skin treatment compositions of Examples 2 to 5 were those with the effect of preventing skin roughness and improving skin toughness, quick in absorption into the skin, and superior in the moisturizing effect.

The external skin treatment composition of the present invention is an external skin treatment composition which improves skin roughness, is quickly absorbed into the skin, and is superior in the moisturizing effect.

We claim:

1. A method for reducing the roughness of skin which comprises applying thereto an amount effective therefor of a composition selected from the group consisting of an aqueous solution, a solubilized composition, an emulsion, a powder, an oil-in-water composition, a gel, a two layer mixture of water and oil, a two-layer mixture of water and powder, and a three-layer mixture of water, oil and powder, each composition comprising 0.1 to 30% by weight of erythritol, 0.0001 to 0.5% by weight of hydrogenated lecithin, and 0.0001 to 0.5% by weight of a cholesterol which has been modified by a polvoxyethylene polyether.

2. A method as claimed in claim 1, wherein the number of moles of oxyethylene in the polyoxyethylene polyester is 5 to 70 moles per 1 mole of the cholesterol.

3. A method as claimed in claim 1, wherein the cholesterol which has been modified by a polyoxyethylene polyether is a polyoxyethylene (30) cholesterol ether having 30 moles of oxyethylene per 1 mole thereof.

4. A method as claimed in claim 1, wherein the content of the erythritol is 0.5 to 20% by weight, based on the weight of the external skin treatment composition.

5. A method as claimed in claim 1, wherein the content of the hydrogenated lecithin is 0.0005 to 0.5% by weight, based on the weight of the external skin treatment composition.

6. A method as claimed in claim 1, wherein the content of a cholesterol which has been modified by a polyoxyethylene polyether is 0.0005 to 0.5% by weight based on the weight of the external skin treatment composition.

7. A method of softening stratum corneum which comprises applying thereto an amount effective therefor of a composition selected from the group consisting of an aqueous solution, a solubilized composition, an emulsion, a powder, an oil-in-water composition, a gel, a two layer mixture of water and oil, a two-layer mixture of water and powder, and a three-layer mixture of water, oil and powder, each composition comprising 0.1 to 30% by weight of erythritol, 0.0001 to 0.5% by weight of hydrogenated lecithin, and 0.0001 to 0.5% by weight of a cholesterol which has been modified by a polyoxyethylene polyether.

8. A method as claimed in claim 7, wherein the number of moles of oxyethylene in the polyoxyethylene polyether is 5 to 70 moles per 1 mole of the cholesterol.

9. A method as claimed in claim 7, wherein the cholesterol which has been modified by a polyoxyethylene polyether is polyoxyethylene (30) cholesterol ether having 30 moles of oxyethylene per 1 mole thereof.

10. A method as claimed in claim 7, wherein the content of the erythritol is 0.5 to 20% by weight, based on the weight of the external skin treatment composition.

11. A method as claimed in claim 7, wherein the content of the hydrogenated lecithin is 0.0005 to 0.5% by weight, based on the weight of the external skin treatment composition.

12. A method as claimed in claim 7, wherein the content of a cholesterol which has been modified by a polyoxyethylene polyether is 0.0005 to 0.5% by weight based on the weight of the external skin treatment composition.

* * * * *

UNITED STATES PATENT AND TRADEMARK OFFICE
CERTIFICATE OF CORRECTION

PATENT NO : 5,753,242
DATED : May 19, 1998
INVENTOR(S): Fumiaki Nakamura, et al.

It is certified that error appears in the above-identified patent and that said Letters Patent is hereby corrected as shown below:

Title Page [56] "References Cited"    Before "5/94 Ziegler" delete "5310555" and insert --5310556--

Column 9, Claim 1, Line 14    After "Modified by a" delete "polvoxyethylene" and substitute --polyoxyethylene--

Column 9, Claim 2, Line 16    After "polyoxyethylene" and before "is 5" delete "polyester" and substitute --polyether--

Signed and Sealed this

Twenty-third Day of November, 1999

Attest:

Q. TODD DICKINSON

*Attesting Officer*    *Acting Commissioner of Patents and Trademarks*